US012059419B2

(12) United States Patent
Jeon et al.

(10) Patent No.: US 12,059,419 B2
(45) Date of Patent: Aug. 13, 2024

(54) PHARMACEUTICAL COMPOSITION COMPRISING PHTHALAZINONE DERIVATIVES

(71) Applicant: IDIENCE CO., LTD., Seoul (KR)

(72) Inventors: Daeun Jeon, Gyeonggi-do (KR); Jeongeun Lee, Gyeonggi-do (KR); Jinhyuk Jeong, Gyeonggi-do (KR); Kyuho Jeong, Gyeonggi-do (KR)

(73) Assignee: IDIENCE CO., LTD., Seoul (KR)

(*) Notice: Subject to any disclaimer, the term of this patent is extended or adjusted under 35 U.S.C. 154(b) by 203 days.

(21) Appl. No.: 17/072,233

(22) Filed: Oct. 16, 2020

(65) Prior Publication Data

US 2022/0117961 A1 Apr. 21, 2022

(51) Int. Cl.
| | |
|---|---|
| *A61K 31/502* | (2006.01) |
| *A61K 9/28* | (2006.01) |
| *A61K 47/26* | (2006.01) |
| *A61K 47/32* | (2006.01) |
| *A61K 47/38* | (2006.01) |

(52) U.S. Cl.
CPC .............. *A61K 31/502* (2013.01); *A61K 9/28* (2013.01); *A61K 47/26* (2013.01); *A61K 47/32* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 7,834,015 B2 | 11/2010 | Jones et al. | |
| 8,129,380 B2 | 3/2012 | Menear et al. | |
| 8,188,084 B2 | 5/2012 | Jones et al. | |
| 9,187,430 B2 | 11/2015 | Ji et al. | |
| 9,682,973 B2 | 6/2017 | Kang et al. | |
| 9,844,550 B2 | 12/2017 | Kang et al. | |
| 2005/0059663 A1 | 3/2005 | Martin et al. | |
| 2008/0161280 A1 | 7/2008 | Gandhi et al. | |
| 2012/0071684 A1 | 3/2012 | Walling et al. | |
| 2015/0225401 A1 | 8/2015 | Wu et al. | |
| 2016/0222003 A1* | 8/2016 | Kang | A61P 43/00 |
| 2019/0177281 A1 | 6/2019 | Rajan et al. | |

FOREIGN PATENT DOCUMENTS

| | | |
|---|---|---|
| CN | 101925595 A | 12/2010 |
| CN | 102372706 A | 3/2012 |
| CN | 103130723 A | 6/2013 |
| EP | 1633724 B1 | 5/2011 |
| EP | 2799435 A1 | 11/2014 |
| JP | 2006-519827 A | 8/2006 |
| JP | 2009-538896 A | 11/2009 |
| JP | 2009-538897 A | 11/2009 |
| JP | 2010-514785 A | 5/2010 |
| KR | 20170037116 A | 4/2017 |
| WO | WO-2000/36576 A1 | 6/2000 |
| WO | WO-02/36576 A1 | 5/2002 |
| WO | WO-03/093261 A1 | 11/2003 |
| WO | WO-2004/080976 A1 | 9/2004 |
| WO | WO-2007/138351 A2 | 12/2007 |
| WO | WO-2007/138355 A1 | 12/2007 |
| WO | WO-2008083027 A1 | 7/2008 |
| WO | WO-2009/063244 A1 | 5/2009 |
| WO | WO-2009093032 A1 | 7/2009 |
| WO | WO-2009/112832 A1 | 9/2009 |
| WO | WO-2012/014221 A1 | 2/2012 |
| WO | WO-2012/019427 A1 | 2/2012 |
| WO | WO-2012/019430 A1 | 2/2012 |
| WO | WO-2012019426 A1 | 2/2012 |
| WO | WO-2012/071684 A1 | 6/2012 |
| WO | WO-2012/072033 A1 | 6/2012 |
| WO | WO-2013/078771 A1 | 6/2013 |

OTHER PUBLICATIONS

Pharmapproach, Excipients Used in the Manufacture of Tablets, Jun. 22, 2020) (Year: 2020).*
Merwe et al. (The role of Functional Excipients in Solid Oral Dosage Forms to Overcome Poor Drug Dissolution and Bioavailability, Pharmaceutics 2020). (Year: 2020).*
Chaudhari, et al (IJAPBC, Pharmaceutical Excipients: A Review—vol. 1(1), Jan.-Mar. 2012). (Year: 2012).*
Campbell et al., "The Degradation Chemistry of GSK2879552: Salt Selection and Microenvironmental pH Modulation to Stabilize a Cyclopropyl Amine." Journal of Pharmaceutical Sciences vol. 108, Issue 9, 2019, pp. 2858-2864.
International Search Report of International Application No. PCT/IB2020/000318 mailed Jan. 18, 2021, 8 pages.
International Search Report of International Application No. PCT/IB2020/000324 mailed Jan. 18, 2021, 7 pages.
Lee, et al., "A comparative preclinical study of PARP inhibitors demonstrates superb properties for IDX-1197," AACR Annual Meeting 2018, Apr. 14-18, 2018, Chicago, Illinois, USA.
Lee, et al., "Development of IDX-1197, a novel, selective, and highly potent PARP inhibitor," 28th AACR-NCI EORTC Molecular Targets and Cancer Therapeutics Conference in Philadelphia, Pennsylvania, USA; Oct. 26-30, 2017.
McMahon "VEGF Receptor Signaling in Tumor Angiogenesis," The Oncologist, (2000), vol. 5 (Suppl. 1): 3-10.
Pinedo et al., "Translational Research: The Role of VEGF in Tumor Angiogenesis," The Oncologist, (2000), vol. 5, (Suppl 1): 1-2.
Tajbakhsh, et al., "Catalyst-Free One-Pot Reductive Alkylation of Primary and Secondary Amines and N,N-Dimethylation of Amino Acids Using Sodium Borohydride in 2,2,2-Trifluoroethanol," sYNTHESIS, (2011), No. 3: 0490-0496.
Written Opinion of International Patent Application No. PCT/IB2020/000318 mailed Jan. 18, 2021, 10 pages.
Written Opinion of International Patent Application No. PCT/IB2020/000324 mailed Jan. 18, 2021, 8 pages.
Ye et al., "Design, Synthesis, and Biological Evaluation of a Series of Benzo[de][1,7]naphthyridine-7(8H)—ones Bearning a Functionalized Longer Chain Appendage as Novel PARP1 Inhibitors," J. Med. Chem., 2013, 56:2885-2903.

(Continued)

*Primary Examiner* — Melissa S Mercier
(74) *Attorney, Agent, or Firm* — Sughrue Mion, PLLC

(57) ABSTRACT

The present invention relates to stable pharmaceutical composition comprising phthalazinone derivatives having good activity as poly (ADP-ribose) polymerase inhibitors.

23 Claims, No Drawings

(56) References Cited

OTHER PUBLICATIONS

Zhu, et al., "Discovery and SAR of orally efficacious letrahydropyridopyridazinone PARP inhibitors for the treatment of cancer," Bioorganic & Medicinal Chemistry, (2012), vol. 20, No. 15:4635-4645.
International Search Report and Written Opinion mailed Jul. 8, 2021 in International (PCT) Application No. PCT/IB2020/000864.

* cited by examiner

PHARMACEUTICAL COMPOSITION COMPRISING PHTHALAZINONE DERIVATIVES

TECHNICAL FIELD

The present invention relates to a pharmaceutical composition having improved stability comprising phthalazinone derivatives, which are capable of inhibiting poly (ADP-ribose) polymerase activity.

BACKGROUND

Depending on the physical and chemical properties of the active pharmaceutical ingredient, certain pharmaceutical compositions are difficult to manufacture and maintain stability, as the active pharmaceutical ingredient can interact with commonly used pharmaceutical excipients. In addition, it is important to maintaining the safety and efficacy of a pharmaceutical composition throughout its expected shelf life, e.g., total expected time for manufacture, distribution, storage, and administration to a patient.

U.S. Pat. No. 9,682,973 discloses an inhibitor of poly (ADP-ribose) polymerase ("PARP") having antineoplastic activity, wherein the PARP inhibitor is characterized by Formula 1 below or a pharmaceutically acceptable salt thereof. Formula 1 can also be characterized under IUPAC (International Union of Pure and Applied Chemistry) nomenclature as 4-[3-(3-[(cyclopropylamino)methyl]azetidine-1-carbonyl)-4-fluorobenzyl]phthalazin-1(2H)-one. In particular, a hydrochloric acid salt of the compound of Formula 1 is one of the promising candidates as an antineoplastic agent.

[Formula 1]

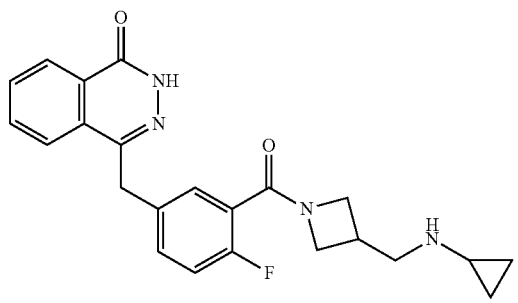

However, during the research and development of a pharmaceutical composition comprising an active pharmaceutical ingredient of Formula 1 or its salt, certain compositions using commonly used excipients were found to be less stable.

SUMMARY OF THE INVENTION

The present invention provides a stable pharmaceutical composition comprising an active pharmaceutical ingredient of Formula 1 or a pharmaceutically acceptable salt thereof.

In one embodiment, the present invention provides a pharmaceutical composition comprising an active pharmaceutical ingredient of Formula 1 or a pharmaceutically acceptable salt thereof and at least one pharmaceutically acceptable excipient, wherein the composition has a pH from about 2.6 to about 6.74 when measured in a 1% (w/v) aqueous suspension:

<Formula 1>

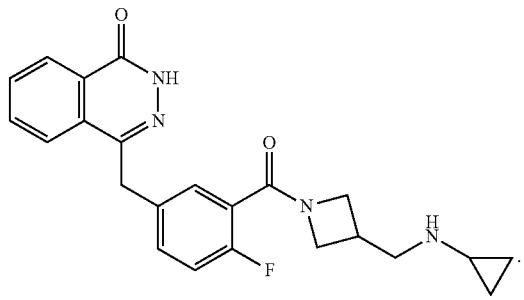

The active pharmaceutical ingredient may be a hydrochloric acid salt of Formula 1.

In another embodiment, the pharmaceutically acceptable excipients may be a diluent, a binder, a disintegrant, a lubricant, or any combination thereof.

In some embodiments, the composition comprises from about 40 to about 90 wt % of the diluent based on the total weight of the composition; from about 0.1 to about 30 wt % of the binder based on the total weight of the composition; from about 1 to about 40 wt % of the disintegrant based on the total weight of the composition; and from about 0.5 to about 40 wt % of the lubricant based on the total weight of the composition.

In some embodiments, the diluent is selected from the group consisting of lactose hydrate, anhydrous lactose, mannitol, sorbitol, microcrystalline cellulose, dibasic calcium phosphate hydrate, or any combination thereof; the binder is selected from the group consisting of hydroxypropyl cellulose (HPC) and Povidone, or any combination thereof; the disintegrant is selected from the group consisting of carmellose, Crospovidone, croscarmellose sodium, sodium starch glycolate, carboxymethylcellulose (CMC), CMC-Ca, low substituted hydroxypropyl cellulose, corn starch, and polacrilin potassium, or any combination thereof; and the lubricant is selected from the group consisting of colloidal silicon dioxide, magnesium stearate, sodium stearyl fumarate, talc, stearic acid or any combination thereof.

The present invention also provides a solid oral dosage form comprising a compound of Formula I:

(I)

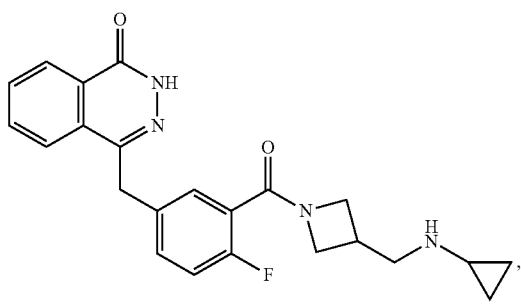

or a pharmaceutically acceptable salt thereof; and at least one excipient selected from the group consisting of a diluent, a binder, a disintegrant, a lubricant, and any combination thereof.

Also provided herein is a stable solid oral dosage form comprising a pharmaceutically acceptable excipient and a compound of Formula I:

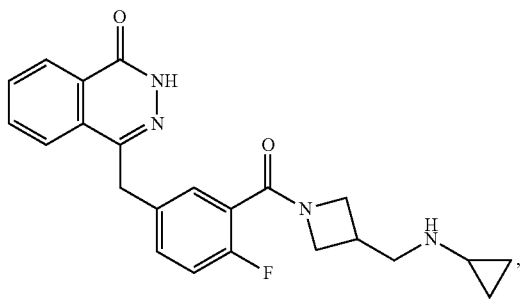

(I)

or a pharmaceutically acceptable salt thereof, wherein the oral dosage form maintains at least 99 wt % of the compound of Formula I upon storage under conditions of 20° C. at 75% relative humidity for at least 1 month.

In one embodiment, the solid oral dosage from is a tablet.

In some embodiments, the solid oral dosage form comprises from about 40 to about 90 wt % of the diluent based on the total weight of the composition; from about 0.1 to about 30 wt % of the binder based on the total weight of the composition; from about 1 to about 40 wt % of the disintegrant based on the total weight of the composition; and from about 0.5 to about 40 wt % of the lubricant based on the total weight of the composition.

In an embodiment, provided herein is a method for preparing a pharmaceutical composition having a pH of about 2.6 to about 6.74 measured in 1% w/v Aqueous Suspension, comprising: (a) mixing a compound of Formula 1 below or a pharmaceutically acceptable salt thereof as an active ingredient, with at least one pharmaceutically acceptable excipients to obtain a blend <Formula 1>

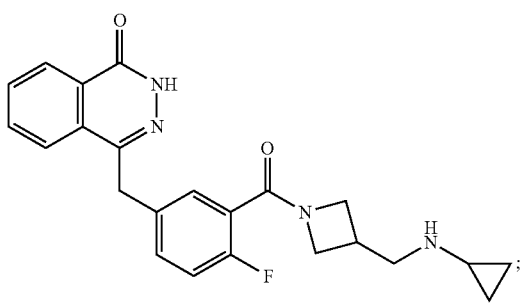

and (b) directly compressing the blend.

In an embodiment, provided herein is a product obtained from the method described herein.

DETAILED DESCRIPTION

The present invention provides a pharmaceutical composition comprising an active ingredient of Formula 1 below or a pharmaceutically acceptable salt thereof, and at least one pharmaceutically acceptable excipient, wherein the composition has a pH from about 2.6 to about 6.74 when measured in a 1% w/v Aqueous Suspension.

<Formula 1>

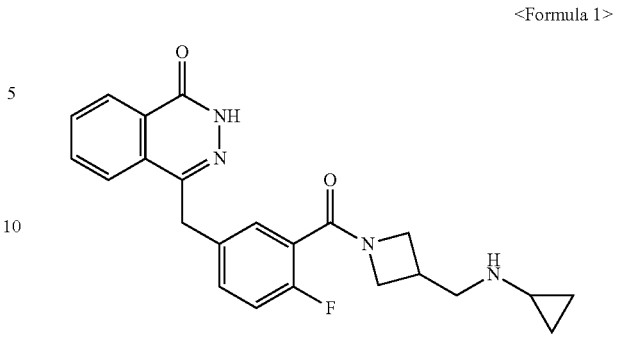

As provided in more detailed in the examples, experimental results show a significantly lower amount of degradation of the active ingredient of Formula 1 during long-term storage when the pH of a composition comprising an active pharmaceutical ingredient of Formula 1 or a pharmaceutically acceptable salt thereof is adjusted to be within a pre-determined range. The resulting pharmaceutical compositions have improved stability during the expected normal shelf life of the composition.

The pH of the pharmaceutical composition is measured by preparing an aqueous suspension of the composition in a 1% w/v (weight by volume) Aqueous Suspension at room temperature prepared according to Experimental Example 1. The method of measuring pH is well known to a person skilled in the pharmaceutical composition arts. For example, the pH of a subject substance is measured by dissolving the substance in water in a concentration of 1% w/v to obtain an aqueous suspension prepared according to Experimental Example 1 and then followed by measuring the pH of the suspension. The pH value can be determined by using any standard technology.

The pharmaceutical compositions of the present invention may have a pH of about 2.6 to about 6.74, preferably, about 2.9 to about 6.5, more preferably, about 2.95 to about 4.95. In some embodiments, when measured by preparing an aqueous suspension of the composition in a 1% w/v (weight by volume) Aqueous Suspension, the pH of the pharmaceutical composition is between about 2 to about 8 (e.g., between about 2 and about 7.5, between about 2 and about 7, between about 2 and about 6.5, between about 2 and 6, between about 2 and about 5.5, between about 2 and about 5, between about 2 and about 4.5, between about 2.5 and about 7.5, between about 2.5 and about 7, between about 2.5 and about 6.5, between about 2.5 and about 6, between about 2.5 and about 5.5, between about 2.5 and about 5, between about 2.5 and about 4.5), or any specific value within said range. In some embodiments, when measured by preparing an aqueous suspension of the composition in a 1% w/v (weight by volume) Aqueous Suspension, the pH of the pharmaceutical composition is preferably between about 3 to about 8 (e.g., between about 3 and about 7.5, between about 3 and about 7, between about 3 and about 6.5, between about 3 and about 6, between about 3 and about 5.5, between about 3 and about 5). The pharmaceutical compositions of the present invention may have a pH in any of the above specific ranges, i.e., without the word "about" in front of the pH values.

I. Definitions

The term "active pharmaceutical ingredient of Formula 1" may also be referenced as "Compound 1" or "the present compound." Similarly, "a salt of the active pharmaceutical ingredient of Formula 1" may also be referenced as "a salt of Compound 1" or "a salt of the present compound". For example, an active pharmaceutical ingredient of Formula 1 in the form of a hydrochloric acid salt may be referenced as "a hydrochloric acid salt of Compound 1" or "a hydrochloric acid salt of the present compound".

"A pharmaceutically acceptable salt" herein may be prepared by any suitable method available in the art, for example, by treating an active pharmaceutical ingredient of Formula 1 in a free base form with an inorganic acid. Examples of useful inorganic acids include, but are not limited to, hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. A hydrochloric acid salt of the active pharmaceutical ingredient of Formula 1 is most preferable.

As used herein, "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The terms "stable" and "stability" herein means that a pharmaceutical composition is stable, for example, with respect to heat, light, temperature, and/or humidity. For example, the pharmaceutical composition of the present invention is stable when that the amount of total impurities or the amount of M1 impurity of the active ingredient (the "M1 Impurity") comprised in a pharmaceutical composition is a specific percentage or less after storage of the pharmaceutical composition under certain conditions. The M1 Impurity is any inactive form of the active ingredient, e.g., a synthetic intermediate, a metabolic intermediate, a by-product, or a degradation product of the active ingredient.

The total impurity measured by HPLC may be defined as having a relative retention time ("RRT") of about 0.11 to 2.10 with respect to a peak for Compound 1, more specifically, about 0.90, about 1.12, about 1.35, or about 1.38. The M1 Impurity may be defined as having a RRT of about 0.90 relative to the peak for Compound 1. As is well known in the art, the RRT values in HPLC can have an experimental error of ±10% of the indicated value. As a result, the values described above should be interpreted in view of the experimental error.

As used herein, a "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)). In certain embodiments, the subject is a human. In certain embodiments, the subject is a non-human animal. The terms "human," "patient," and "subject" are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term. For pH values, the term "about" will mean up to plus or minus 0.5% of the pH value.

As used herein, an "assay" refers to a specific, stability-indicating procedure that determines the content of the drug substance. For example, an assay can be a chromagraphic method (e.g., HPLC) involving use of a reference standard.

As used herein, "crystalline" refers to a solid having a highly regular chemical structure, i.e., having long range structural order in the crystal lattice. The molecules are arranged in a regular, periodic manner in the 3-dimensional space of the lattice. In particular, a crystalline form may be produced as one or more single crystalline forms.

As used herein, an "excipient" is a pharmaceutically acceptable inactive ingredient that is commonly used for preparing a pharmaceutical formulation. Examples of appropriate excipients can be found in Sheskey et al., *Handbook of Pharmaceutical Excipients*, Eighth Ed., authored (Pharmaceutical Press 2017), which is incorporated herein by reference in its entirety. Excipients can be categorized by their functional characteristics, such as a diluent, a binder, a disintegrant, a superdisintegrant, a lubricant, a pH control agent, a glidant, a filler, a stabilizing agent, an anti-oxidant, and a film-coating agent. However, as is well-known in the art, a particular excipient can be categorized into more than one of the previously listed functional groups depending on when and how the excipient is used, e.g., an excipient can be categorized as a disintegrant in one formulation and a binder in another formulation. In some cases, a particular excipient can be multi-functional, i.e., be categorized as belonging to more than functional group within the same formulation. General considerations in the formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of*

*Pharmacy*, 21st Edition (Lippincott Williams & Wilkins, 2005), both of which are incorporated herein by reference in their entirety.

As used herein, a "binder" is an excipient that imparts a pharmaceutical composition with enhanced cohesion or tensile strength (e.g., hardness). Examples of binders include dibasic calcium phosphate, sucrose, corn (maize) starch, microcrystalline cellulose, and modified cellulose (e.g., hydroxymethyl cellulose).

As used herein, a "diluent" is an excipient that adds bulkiness to a pharmaceutical composition. Examples of diluents include lactose, sorbitol, celluloses, calcium phosphates, starches, sugars (e.g., mannitol, sucrose, or the like) or any combination thereof.

As used herein, a "disintegrant" is an excipient that hydrates a pharmaceutical composition and aids in tablet dispersion. Examples of disintegrants include sodium croscarmellose and/or sodium starch glycolate.

As used herein, a "lubricant" is an excipient that is added to pharmaceutical compositions that are pressed into tablets. The lubricant aids in compaction of granules into tablets and ejection of a tablet of a pharmaceutical composition from a die press. Examples of lubricants include magnesium stearate, stearic acid (stearin), hydrogenated oil, sodium stearyl fumarate, or any combination thereof.

II. Compounds

Described herein are pharmaceutical compositions comprising compounds that are useful for preventing and/or treating a disease, disorder, or condition, e.g., a disease, disorder, or condition relating to cancer.

In one aspect, the present disclosure is directed to a pharmaceutical composition comprising Formula I:

(Formula I)

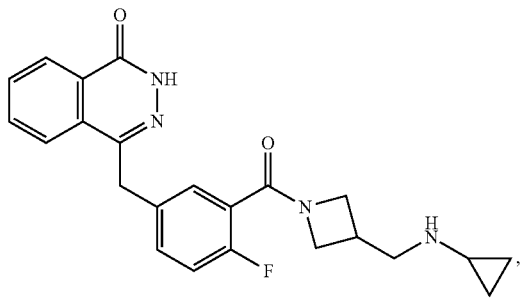

or a pharmaceutically acceptable salt thereof.

Formula I, or a pharmaceutically acceptable salt thereof, can be obtained by following any method known to the person of ordinary skill in the art, including by following the preparation methods disclosed in U.S. Pat. No. 9,682,973, which is incorporated by reference herein in its entirety.

Crystalline forms of phthalazinone compound are also disclosed in U.S. patent application Ser. No. 16/858,158 filed on Apr. 24, 2020, which application is incorporated by reference herein in its entirety.

In some embodiments, a hydrochloride salt of Formula I is in a crystalline form exhibiting an X-ray powder diffraction (XRPD) pattern comprising peaks at diffraction angles 2θ±0.2° values of 13.7°, 15.9°, and 24.1° (hereinafter referred to as "Crystalline Form A"). In some embodiments, Crystalline Form A may exhibit an XRPD pattern comprising peaks at three or more and preferably four or more 2θ±0.2° values selected from the group consisting of 9.1°, 11.9°, 13.2°, 13.7°, 15.9°, 16.8°, 18.1°, 23.2°, 24.1°, 25.5°, and 26.6°. In particular, Crystalline Form A may exhibit an XRPD pattern comprising peaks at 2θ±0.2° values of 9.1°, 13.2°, 13.7°, 15.9°, 16.8°, 24.1°, and 26.6°. In more particularity, Crystalline Form A may exhibit an XRPD pattern comprising peaks at 2θ±0.2° values of 9.1°, 11.9°, 13.2°, 13.7°, 15.9°, 16.8°, 18.1°, 23.2°, 24.1°, 25.5°, and 26.6°. The XRPD pattern may be obtained using any method known to the skilled artisan, including by irradiating with a Cu-Kα light source, for example, a D8 Advance (Bruker ASX, Germany) analyzer. The Cu-Kα light source may have a wavelength of 1.54056 Å.

III. Dosage Forms and Compositions

In one aspect, the present disclosure features dosage forms or compositions useful for preventing and/or treating a disease, disorder, or condition described herein, e.g., cancer.

This invention provides pharmaceutical compositions that contain, as the active ingredient, a compound described herein (e.g., Compound 1), or a pharmaceutically acceptable salt thereof, and one or more pharmaceutically acceptable excipients, including, but not limited to, any one or more of the following: carriers, diluents, binders, disintegrants, and lubricants. The pharmaceutical compositions may be administered alone or in combination with other therapeutic agents.

The pharmaceutical compositions of the present invention may comprise from about 0.1 to about 70 wt % and preferably about 1 to 40 wt % based on the total weight of the composition of Compound 1 or a pharmaceutically acceptable salt thereof. In terms of total amounts, the pharmaceutical compositions of the present invention comprise from about 1 to about 400 mg per unit dosage and preferably about 10 to about 240 mg of Compound 1 or a pharmaceutically acceptable salt thereof. Other embodiments of the pharmaceutical compositions include 10 mg, 20 mg, 40 mg, 80 mg, 160 mg, or 240 mg of Compound 1 or a pharmaceutically acceptable salt thereof. The amounts above are based on the free base from of Compound 1.

In one embodiment, the compositions of the present invention have a preferred threshold of the total impurities in the pharmaceutical composition after stability testing. After storing the pharmaceutical composition of the present invention at temperatures from 25° C. to 70° C. (e.g., 25° C., 40° C., 50° C., 60° C., or 70° C.) and relative humidity (RH) from 60% to 75% (e.g., 60% or 75%) for about 1 week to 12 months (e.g., 1 week, 2 weeks, 4 weeks, 1 month, 3 months, 6 months, or 12 months), the content of the total impurities of the pharmaceutical composition measured by HPLC is 1.50% or less, preferably, 1.0% or less, more preferably, 0.80% or less, and more preferably, 0.40% or less, based on the total weight of the pharmaceutical composition. For example, the content of the total impurities of the active ingredient may be 1.0% or less, after the storage of the composition of the present invention at 50° C. and 75% relative humidity for 1 month.

In another embodiment, the compositions of the present invention have a preferred threshold of M1 Impurity in the pharmaceutical composition after stability testing. After storing the pharmaceutical composition of the present invention at temperatures from 25° C. to 70° C. (e.g., 25° C., 40° C., 50° C., 60° C., or 70° C.) and relative humidity (RH) from 60% to 75% (e.g., 60% or 75%) for about 1 week to 12 months (e.g., 1 week, 2 weeks, 4 weeks, 1 month, 3 months, 6 months, or 12 months), the content of M1 Impurity of the active ingredient measured by HPLC is 0.50% or less, preferably, 0.4% or less, more preferably, 0.20% or less, based on the total weight of the pharmaceutical composition. For example, the content of M1 Impurity of the active ingredient may be 0.50% or less, after the storage of the composition of the present invention at 50° C. and 75% relative humidity for 1 month.

The pharmaceutical composition of the present invention have at least one pharmaceutically acceptable excipient. The type and amount of the excipient may appropriately be selected to the extent that the pharmaceutical composition of the present invention meets a pH of about 2.6 to about 6.74 measured in a 1% w/v Aqueous Suspension prepared according to Experimental Example 1. Further, excipients may improve the processing properties of a formulation, for example, fluidity and/or aggregation to allow better compression of the pharmaceutical composition. It is also preferable to select excipients in consideration of the dissolution rate of the pharmaceutical composition.

In one embodiment, the pharmaceutical composition of the present invention comprises a diluent, a binder, a disintegrant, a lubricant, or any combination thereof.

The diluent may include, but are not limited to, the following: lactose, such as anhydrous lactose or lactose hydrate (e.g., Flowlac 100); microcrystalline cellulose (e.g., Avicel pH-101 or Pharmacel 101); dibasic calcium phosphate hydrate (e.g. carmellose, EMCOMPRESS); mannitol, such as D-mannitol (e.g., Mannogem EZ); sorbitol, such as D-sorbitol (e.g., XTAB 200S); refined sugar, such as compressible sugar, dextrate, dextrin, or dextrose; pulverized cellulose; or any combination thereof. Preferably, the diluent of the present invention may be lactose hydrate, anhydrous lactose, mannitol, sorbitol, microcrystalline cellulose, dibasic calcium phosphate hydrate, or any combination thereof, more preferably, lactose hydrate, mannitol, sorbitol, microcrystalline cellulose, or any combination thereof, and, most preferably, lactose hydrate, microcrystalline cellulose, or any combination thereof.

In some embodiments, the diluent is lactose hydrate. In some embodiments, the diluent is anhydrous lactose. In some embodiments, the diluent is microcrystalline cellulose. In some embodiments, the diluent is dibasic calcium phosphate hydrate. In some embodiments, the diluent is mannitol. In some embodiments, the diluent is sorbitol. In some embodiments, the diluent is refined sugar. In some embodiments, the diluent is pulverized cellulose.

The diluent may be comprised in an amount of about 40 to about 90 wt %, preferably, about 70 to about 90 wt %, based on the total weight of the composition.

The binder may include, but are not limited to, the following: hydroxypropyl cellulose (e.g., HPC-L or HPC-EXF), Povidone (e.g., K-30); hydroxyethyl cellulose; hydroxypropylmethyl cellulose (e.g., METHOCEL); sucrose; dextrose; corn syrup; polysaccharide; or any combination thereof. Preferably, the binder of the present invention may be hydroxypropyl cellulose, Povidone, or any combination thereof, and, more preferably, hydroxypropyl cellulose.

In some embodiments, the binder is hydroxypropyl cellulose. In some embodiments, the binder is Povidone. In some embodiments, the binder is hydroxyethyl cellulose. In some embodiments, the binder is sucrose. In some embodiments, the binder is dextrose. In some embodiments, the binder is corn syrup. In some embodiments, the binder is polysaccharide.

The binder may be comprised in an amount of about 0.1 to about 30 wt %, preferably, about 0.5 to about 20 wt %, based on the total weight of the composition.

The disintegrant may include, but are not limited to, the following: carboxymethylcellulose (CMC; referred to as carmellose, e.g., NS-300); calcium carboxymethylcellulose (CMC-Ca); sodium carboxymethylcellulose (CMC-Na); low substituted hydroxypropyl cellulose (e.g., Grade LH-11, LH-21, LH-31, etc. which have 11% of hydroxypropoxy content); corn starch; polacrilin potassium; pregelatinized starch; clays; alginate; gum; or any combination thereof. Preferably, the disintegrant of the present invention may be CMC, CMC-Ca, CMC-Na, low substituted hydroxypropyl cellulose, corn starch, polacrilin potassium, or any combination thereof, and, more preferably, CMC.

In some embodiments, the disintegrant is carboxymethylcellulose. In some embodiments, the disintegrant is calcium carboxymethylcellulose. In some embodiments, the disintegrant is sodium carboxymethylcellulose. In some embodiments, the disintegrant is low substituted hydroxypropyl cellulose. In some embodiments, the disintegrant is corn starch. In some embodiments, the disintegrant is polacrilin potassium. In some embodiments, the disintegrant is pregelatinized starch. In some embodiments, the disintegrant is clay. In some embodiments, the disintegrant is alginate. In some embodiments, the disintegrant is gum.

The disintegrant may be comprised in an amount of about 1 to about 40 wt %, preferably, about 3 to about 20 wt %, based on the total weight of the composition.

The lubricant may include, but are not limited to, the following: colloidal silicon dioxide; talc; stearic acid' magnesium stearate' calcium stearate; sodium stearyl fumarate (e.g., Pruv); or any combination thereof. Preferably, the lubricant of the present invention may be colloidal silicon dioxide, magnesium stearate, sodium stearyl fumarate, talc, stearic acid, or any combination thereof, and, more preferably, colloidal silicon dioxide, magnesium stearate, or any combination thereof.

In some embodiments, the lubricant is colloidal silicon dioxide. In some embodiments, the lubricant is talc. In some embodiments, the lubricant is stearic acid' magnesium stearate' calcium stearate. In some embodiments, the lubricant is sodium stearyl fumarate.

The lubricant may be comprised in an amount of about 0.5 to about 40 wt %, preferably, about 1 to about 20 wt % based on the total weight of the composition.

In another embodiment, the pharmaceutical composition of the present invention may further comprise a pH control agent. When the pH of the pharmaceutical composition is within the range from about 2.6 to 6.74 as measured in 1% w/v Aqueous Suspension prepared according to Experimental Example 1 without any pH control agent, an additional pH control agent would not be required. When the pH of the pharmaceutical composition is beyond the range without any pH control agent, a pH control agent may be appropriately added to adjust pH of the pharmaceutical composition within the pH range. In an exemplary embodiment, when a pharmaceutical composition comprises CMC as the disintegrant (Test Sample 2), the pH in 1% w/v Aqueous Suspension prepared according to Experimental Example 1 is about 4.3, which means that additional pH control agent would not be required to be used. On the other hand, when a pharmaceutical composition comprises polacrilin potassium as the disintegrant, the pH is about 7.97 and the content of impurities increases, thereby becoming unstable (Test Sample 9). In this case, additional use of a pH control agent would be required to fall within the desired range of pH. An increased content of impurities was also found when using CMC-Na (Test Sample 11), and the additional use of a pH control agent may increase stability of the pharmaceutical composition.

Any pH control agent or a combination of pH agents known in the art may be used as long as the desired range of pH is achieved.

In a preferable embodiment, the pH control agent used in the present invention may be a pH control agent having about 1 to about 5, preferably about 1.5 to about 3, and more preferably about 2 to about 2.5 of pH. Herein, the pH of a pH control agent is defined as pH of a solution or suspension obtained when the pH control agent is dissolved or suspended in water in a concentration of 1% w/v at room temperature.

The pH control agent may include, but are not limited to, the following: an acid substance such as, tartaric acid, citric acid, lactic acid, fumaric acid, maleic acid, ascorbic acid, acetic acid, or acid amino acid (e.g., glutamic acid or aspartic acid); an inorganic salt of the acid substance (e.g., alkali metal salt, alkaline earth metal salt, ammonium, etc.); a salt of the acid substance having an organic base (e.g., basic amino acid such as lysine, arginine, meglumine, etc.); and hydrates thereof, solvates thereof, or any combination thereof. Preferably, pH control agent may be citric acid, fumaric acid, maleic acid, or any combination thereof.

The pH control agent may be comprised in an amount of about 0.01 to about 20 wt %, and, preferably, about 0.05 to about 10 wt % based on the total weight of the composition.

In another embodiment, the pharmaceutical composition of the present invention may further comprise a superdisintegrant. The superdisintegrant may include, but are not limited to, the following: Crospovidone; croscarmellose sodium; sodium starch glycolate; natural, modified, or pregelatinized starch; effervescent disintegrating systems; or any combination thereof. Preferably, the superdisintegrant may be Crospovidone, croscarmellose sodium, sodium starch glycolate, or any combination thereof.

In some embodiments, the superdisintegrant is Crospovidone. In some embodiments, the superdisintegrant is croscarmellose sodium. In some embodiments, the superdisintegrant is sodium starch glycolate. In some embodiments, the superdisintegrant is natural, modified, or pregelatinized starch. In some embodiments, the superdisintegrant is effervescent disintegrating systems.

The superdisintegrant may be comprised in an amount of about 0.01 to about 20 wt %, preferably, about 1 to about 10 wt %, more preferably about 1 to about 5 wt % based on the total weight of the composition.

The function or effect of the excipients illustrated above is not absolute, while one excipient may have at least two functions in some cases. For example, some disintegrants may also function as a binder and a filler. Various functions or effects of an excipient may be determined as already known in the art.

Oral administration is a route for administration of compounds in accordance with the invention. Administration may be via capsule or tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

The pharmaceutical composition of the present invention may be in the form of a solid oral dosage form or a solid preparation, such as a tablet, granules, microgranules, a capsule, a pill, and the like. The solid preparation may be, preferably, a tablet, for example, a tablet coated with a film-coating agent. In some embodiments, the pharmaceutical composition can be made into tablets. In some embodiments, the tablets comprising a pharmaceutical composition as described herein can be coated with a film-coating. In some embodiments, the tablets comprising a pharmaceutical composition as described herein can be coated with an enteric coating.

Tablets containing the pharmaceutical composition of the present invention can also be coated with a film. For example, the film is for enteric coating. In some embodiments, the film comprises a cellulosic polymer (e.g. hydroxypropyl cellulose, hydroxypropylmethyl cellulose, methyl cellulose, or any combination thereof). One exemplary film-coating agent may be Opadry® comprising hydroxypropylmethyl cellulose (Hypromellose), e.g., Opadry® White 03B28796.

IV. Methods of Making

The pharmaceutical composition of the present invention may be prepared by any known method or processes, for example, grinding, mixing or blending, granulation, drying, molding (tableting), film coating, crystallization, and the like.

As such, the present invention also provides a method for preparing a pharmaceutical composition having a pH of 2.6 to 6.74 measured in 1% w/v Aqueous Suspension, comprising:

(a) mixing a compound of Formula 1 below or a pharmaceutically acceptable salt thereof as an active ingredient, with at least one pharmaceutically acceptable excipients to obtain a blend;

<Formula 1>

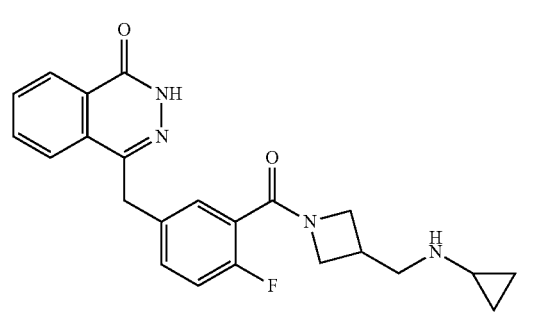

(b) directly compressing the blend.

In one embodiment, the present invention provides a direct compression method for preparing a pharmaceutical composition, comprising the steps of:
(a) pre-blending an active ingredient with some or most of the excipients in a mixer to obtain a pre-blender;
(b) optionally, dry screening the pre-blender via screen to separate cohesive particles and improve content uniformity;

(c) mixing the pre-blender in step (a) or (b) with the remaining excipients in a mixer to obtain a final blender;

(d) compressing and tableting the final blender in step (c) in a tablet press to prepare a tablet core; and (e) optionally, film coating the tablet core of the step (d).

According to one specific embodiment, an active ingredient, a diluent, a binder, a disintegrant, and a lubricant are pre-blended in a diffusion mixer, sieved in a hand screen or screen mill, and again pre-blended in a diffusion mixer, to prepare a blended intermediate composition. Additional lubricant is separately sieved in a hand screen or screen mill, followed by blending with the blended intermediate in a diffusion mixer to prepare a blend. The blend is subject to direct compression in a rotary tablet press to obtain a tablet (plain tablet), followed by adding a film-coating agent, to prepare a film-coated tablet.

Granules of a pharmaceutical composition according to the present invention may be prepared by any methods well known to those skilled in the art. A preferred method for granulating an active ingredient together with excipients includes wet granulation, such as high shear wet granulation or fluid bed wet granulation, and dry granulation which is also referred to as roller compaction.

In the wet granulation process the granulation liquid are the solvent alone or a preparation of one or more binders in a solvent or mixture of solvents. Suitable binders are described hereinbefore. Examples are hypromellose, hydroxypropyl cellulose, povidone and copovidone. Suitable solvents are for example purified water, ethanol, methanol, isopropanol, acetone, preferably purified water, including mixtures thereof. The solvent is a volatile component, which does not remain in the final product. The one or more active ingredients and the other excipients, in particular the one or more diluents and the one or more disintegrants, usually with exception of the lubricant, are premixed and granulated with the granulation liquid, for example using a high shear granulator. The wet granulation step is usually followed by one or more drying and sieving steps. For example, a drying oven or a fluid bed dryer can then be used for drying.

The dried granules are sieved through an appropriate sieve. After optional addition of the other excipients, in particular disintegrant, binder, filler and/or lubricant, the mixture is blended in a suitable blender, for example a free fall blender, followed by addition of the one or more lubricants, for example magnesium stearate, and final blending in the blender.

In one specific embodiment, the present invention provides a wet granulation process for preparing a pharmaceutical composition comprising the steps of:

(a) pre-blending the active ingredient and some or most of the excipients including the binder in a mixer to obtain a pre-blender;

(b) granulating the pre-blender of step (a) by adding the granulation liquid, preferably purified water;

(c) drying the granules of step (b) in a fluidized bed dryer or a drying oven;

(d) optionally dry sieving of the dried granules of step (c);

(e) mixing the dried granules of step (d) with the remaining excipients of lubricant, glidant, and the like in a mixer to obtain the final mixture;

(f) tableting the final mixture of step (e) by compressing it on a suitable tablet press to produce tablets cores; and (g) optionally film-coating of the tablet cores of step (f).

In another embodiment, the present invention provides a dry granulation process for preparing a pharmaceutical composition comprising the steps of:

(a) mixing an active ingredient with either all or a portion of the excipients in a mixer;

(b) compaction of the mixture of step (a) on a suitable roller compactor;

(c) changing the ribbons obtained during step (b) to granule, preferably, small granules by suitable milling or sieving steps;

(d) optionally mixing the granules of step (c) with the remaining excipients in a mixer to obtain the final mixture;

(e) tabletting the granules of step (c) or the final mixture of step (d) by compressing it on a suitable tablet press to produce the tablet cores; and (f) optionally film-coating of the tablet cores of step (e).

The present invention also provides a pharmaceutical composition such as a tablet, which can be obtained by the following method.

Granules and microgranules may be prepared by granulating based on the same method as one used for a tablet (e.g., wet or dry granulation). Otherwise, they may be prepared by spraying a coating liquid comprising an active ingredient and excipients, especially, a binder such as sucrose, hydroxypropyl cellulose, hydroxypropylmethylcellulose, etc., on sugar spheres, to coat the spheres. As such, the granules may be wet or dry granules.

A capsule is produced by filling capsules made of gelatin, e.g., hydroxypropylmethylcellulose, with the granules or microgranules, or filling capsules made of gelatin, e.g., hydroxypropylmethylcellulose, with the active ingredient together with an excipient (e.g., lactose, sucrose, glucose, starch, saccharose, microcrystalline cellulose, powdered *Glycyrrhiza*, mannitol, sodium hydrogencarbonate, calcium phosphate, calcium sulfate, etc.).

V. Methods of Use and Treatment

One feature of the present disclosure relates to pharmaceutical compositions that can be useful as therapeutic agents for the treatment of diseases improved by PARP inhibition, or cancers caused by generic defect of BRCA1, BRCA2, and ERG fusion gene. In some embodiments, a pharmaceutical composition comprising Formula I as provided by the present disclosure is effective in the treatment of cancer, such as stomach cancer, ovarian cancer, breast cancer. Other embodiments of methods of using the compositions of the present invention can be found in U.S. Pat. No. 9,682,973, which is incorporated herein by reference in its entirety.

Hereinafter, the present invention will be described in more detail by the working examples. However, the examples are provided merely to illustrate the present invention, and not to intended be construed as limiting the present invention.

EXAMPLES

In order that the invention described herein may be more fully understood, the following examples are set forth. The examples described in this application are offered to illustrate the aspects of the invention and their embodiments provided herein and are not to be construed in any way as limiting their scope.

Abbreviations

BRT below reporting threshold
CMC carboxymethyl cellulose
CMC-Ca calcium carboxymethyl cellulose
HDPE high density poly ethylene
HPLC high performance liquid chromatography
HPC hydroxypropylcellulose
ND not determined
RH relative humidity
UV Ultraviolet

Experimental Example 1: Stability Versus Different pHs for Tablets of Test Samples 1 to 9

A hydrochloric acid salt of the present compound and excipients were mixed in accordance with the composition recited in Table 1 below and tableted to prepare a plain uncoated tablet. Each tablet was placed in triple distilled water so that the concentration of the tablet was 1% w/v (weight by volume) and stirred at room temperature using a magnetic stir bar at 1,200 rpm for five (5) minutes to form an aqueous suspension (referenced as "1% w/v Aqueous Suspension"). After allowing the suspension to rest for five (5) minutes, the pH of the suspension was measured at room temperature using a S20 SevenEasy pH meter manufactured by Mettler Toledo. The pH of each tablet prepared in Test Samples 1 to 9 was measured, and the results are presented in Table 1 below.

In addition, the stability of each tablet prepared in Examples 1 to 9 was evaluated. Each tablet was stored at 50° C. at 75% RH (relative humidity) with a desiccant (silica gel) sealed in a HDPE bottle for 2 and 4 weeks, and then the content (%) of M1 Impurity and the content (%) of the total impurities in each a tablet was determined by HPLC.

The HPLC analysis was performed on a detector with the $UV_{max}$ set at or near 280 nm using a C18 column (4.6 mm×15 cm; 5 μm) and mobile phase was a mixture of purified water and formic acid or a mixture of methanol and formic acid. The analysis for M1 Impurity content (%) and the total impurities content (%) were conducted at the initial date (0 days), 2 weeks and 4 weeks. The content (%) of impurities is calculated in the following manner.

Content of $M1$ Impurity (%) =
$$\left(\frac{\text{Peak area of } M1 \text{ Impurity in the sample}}{\text{Total peak area of Sample}}\right) \times 100$$

Content of total impurity (%) =
$$\left(\frac{\text{Sum of the } pieak \text{ area of each impurity in the sample}}{\text{Total peak area of Sample}}\right) \times 100$$

The results are presented in Table 1 below.

TABLE 1

| | | Test Sample | | | | | | | | |
|---|---|---|---|---|---|---|---|---|---|---|
| Function | Ingredient | 1 | 2 | 3 | 4 | 5 | 6 | 7 | 8 | 9 |
| Active ingredient | hydrochloric acid salt of Compound 1 | 21.8 | 21.8 | 21.8 | 21.8 | 21.8 | 21.8 | 21.8 | 21.8 | 21.8 |
| Diluent | lactose hydrate | 254.2 | 254.2 | 254.2 | 268.9 | 268.3 | 266.2 | 254.2 | 254.2 | 254.2 |
| Binder | hydroxypropyl cellulose | 3.0 | 3.0 | 3.0 | 3.0 | 3.0 | 3.0 | 3.0 | 3.0 | 3.0 |
| Disintegrant | carmellose | — | 15.0 | — | — | — | — | — | — | — |
| Disintegrant | polacrilin potassium | — | — | — | — | — | — | — | — | 15.0 |
| Lubricant | colloidal silicon dioxide | 3.0 | 3.0 | 3.0 | 3.0 | 3.0 | 3.0 | 3.0 | 3.0 | 3.0 |
| Lubricant | magnesium stearate | 3.0 | 3.0 | 3.0 | 3.0 | 3.0 | 3.0 | 3.0 | 3.0 | 3.0 |
| pH control agent | citric acid | — | — | 15.0 | — | — | — | — | — | — |
| pH control agent | fumaric acid | — | — | — | 0.3 | 0.9 | 3.0 | 15.0 | — | — |
| pH control agent | maleic acid | — | — | — | — | — | — | — | 15.0 | — |
| Total amount of one tablet (mg) | | 285.0 | 300.0 | 300.0 | 300.0 | 300.0 | 300.0 | 300.0 | 300.0 | 300.0 |
| pH measured in an 1% w/v Aqueous Suspension | | 6.48 | 4.31 | 3.05 | 4.95 | 3.95 | 3.4 | 2.97 | 2.6 | 7.97 |
| M1 Impurity (%) | Initial | 0.01 | 0.02 | 0.01 | 0 | ND | ND | 0.01 | 0.01 | 0.02 |
| Closed, 50° C./ 75% RH | 2 week | 0.15 | 0.13 | 0.04 | 0.17 | 0.16 | 0.11 | 0.03 | 0.01 | 0.58 |
| | 4 week | 0.27 | 0.24 | 0.07 | 0.29 | 0.28 | 0.17 | 0.05 | 0.01 | 0.86 |
| Total impurities (%) | Initial | 0.05 | 0.07 | 0.06 | 0.05 | 0.04 | 0.04 | 0.07 | 0.07 | 0.09 |
| Closed, 50° C./ 75% RH | 2 week | 0.25 | 0.27 | 0.15 | 0.27 | 0.26 | 0.21 | 0.14 | 0.68 | 0.74 |
| | 4 week | 0.36 | 0.36 | 0.2 | 0.38 | 0.38 | 0.36 | 0.19 | 1.09 | 1.08 |

※ ND: Not Determined

The pharmaceutical compositions containing a hydrochloric acid salt of the present compound having a pH in the range of about pH 2.6 to pH 6.48 (Test Samples 1 to 8) exhibited remarkable stability, as shown by the low level of impurities after long-term storage. In particular, the best stability was found around pH 3.0 (Test Samples 3 and 7). On the other hand, when the pH was higher than 7.0, the amount of impurities rapidly increased and stability decreased (Test Samples 9).

It was thus confirmed that the compound of the present invention is stable in the range of about pH 2.6 to pH 6.48.

The pH of each tablet prepared in Test Samples 2 and 10 to 21 was measured as described in Experimental Example 1, and the results are presented in Table 2 and 3 below.

The stability was evaluated for each tablet prepared in Test Samples 2 and 10 to 21, which contained different excipients. After storing each tablet at 50° C. at 75% RH for 1 week at an open state, the content (%) of impurities (M1) in each tablet was measured according to the HPLC method as described in Experimental Example 1. Tables 2 and 3 show the results.

Test Samples 2 and 10-17

TABLE 2

| | | Test Sample | | | | | | | | |
|---|---|---|---|---|---|---|---|---|---|---|
| Function | Ingredient | 2 | 10 | 11 | 12 | 13 | 14 | 15 | 16 | 17 |
| Active ingredient | hydrochloric acid salt of Compound 1 | 21.8 | 21.8 | 21.8 | 21.8 | 21.8 | 21.8 | 21.8 | 21.8 | 21.8 |
| Diluent | lactose hydrate (Flowlac 100) | 254.2 | 254.2 | 254.2 | 224.2 | 251.2 | 251.2 | 245.2 | 245.2 | 245.2 |
| Diluent | microcrystalline cellulose (101) | — | — | — | 30 | — | — | — | — | — |
| Binder | HPC EXF | 3 | 3 | 3 | 3 | — | 6 | 3 | 3 | 3 |
| Binder | Povidone(K-30) | — | — | — | — | 6 | — | — | — | — |
| Disintegrant | Crospovidone | — | — | — | — | — | — | 9 | — | — |
| Disintegrant | croscarmellose sodium | — | — | — | — | — | — | — | 9 | — |
| Disintegrant | sodium starch glycolate | — | — | — | — | — | — | — | — | 9 |
| Disintegrant | carmellose (CMC; NS-300) | 15 | — | — | 15 | 15 | 15 | 15 | 15 | 15 |
| Disintegrant | CMC-Ca | — | 15 | — | — | — | — | — | — | — |
| Disintegrant | CMC-Na | — | — | 15 | — | — | — | — | — | — |
| Lubricant | colloidal silicon dioxide | 3 | 3 | 3 | 3 | 3 | 3 | 3 | 3 | 3 |
| Lubricant | magnesium stearate | 3 | 3 | 3 | 3 | 3 | 3 | 3 | 3 | 3 |
| Total amount of one tablet (mg) | | 300 | 300 | 300 | 300 | 300 | 300 | 300 | 300 | 300 |
| pH measured in an 1% w/v Aqueous Suspension | | 4.31 | 5.96 | 7.04 | 4.56 | 4.44 | 4.58 | 4.8 | 5.74 | 5.27 |
| M1 Impurity (%) | Initial | BRT | BRT | BRT | BRT | BRT | BRT | BRT | BRT | BRT |
| Open, 50° C./75% RH | 1 week | BRT | 0.18 | 0.68 | 0.07 | BRT | BRT | 0.08 | BRT | BRT |

※ BRT (below reporting threshold)

Experimental Example 2: Stability Based on Different Excipients for Tablets of Test Samples 2 and 10 to 21

Based on the preparation methods described in Test Samples 1 to 9, a hydrochloric acid salt of the present compound and each additive were mixed according to the composition shown in Tables 2 and 3 below, and tableted to prepare a plain uncoated tablet.

It was confirmed from the results above that the tablets of Test Samples 2, 10, and 12 to 17 showed excellent stability, while the stability of the tablets of Example 11 was lower. In Example 11, CMC-Na was used as a disintegrant, where this ingredient was determined to increase the pH of the entire tablet, thereby reducing the stability of the active ingredient.

Test Samples 18 to 21

TABLE 3

| | | Test Samples | | | |
|---|---|---|---|---|---|
| Function | Ingredient | 18 | 19 | 20 | 21 |
| Active Ingredient | hydrochloric acid salt of Compound 1 | 21.8 | 21.8 | 21.8 | 21.8 |
| Diluent | lactose hydrate (Flowlac 100) | 275.2 | 275.2 | 275.2 | 275.2 |

TABLE 3-continued

|  |  | Test Samples | | | |
|---|---|---|---|---|---|
| Function | Ingredient | 18 | 19 | 20 | 21 |
| Binder | hydroxypropyl cellulose (HPC EXF) | 3 | 3 | 3 | 3 |
| Disintegrant | low substitutedhydroxypropyl cellulose (11) | 15.15 | | | |
| Disintegrant | corn starch | | 15.15 | | |
| Disintegrant | polacrilin potassium | | | 15.15 | |
| Disintegrant | carmellose (CMC, NS-300) | | | | 15.15 |
| Lubricant | magnesium stearate | 3 | 3 | 3 | 3 |
| | Total amount of one tablet (mg) | 318.15 | 318.15 | 318.15 | 318.15 |
| | pH measured in an 1% w/v Aqueous Suspension | 6.70 | 6.74 | 7.23 | 4.86 |
| M1 Impurity (%) Open, 50° C./ 75% RH | initial | ND | BRT | BRT | BRT |
| | 1 week | 0.34 | 0.40 | 0.50 | BRT |

※ ND: Not Determined

Test Sample 21 provided the best stability results. Although Test Samples 18-20 were less stable with an increase in M1 Impurity than Test Sample 21, Test Samples 18 and 19 (and 21) still exhibited an M1 Impurity of below the desired level of less than 0.50%. Test Sample 20 was exception.

Experimental Example 3: Stability Based on Different Excipients for Tablets of Test Samples 22 to 33

Based on the preparation methods described in Test Samples 1 to 9, a hydrochloric acid salt of the present compound and each additive were mixed according to the composition shown in Table 4 below, and tableted to prepare a plain uncoated tablet.

The pH of each tablet prepared in Test Samples 22 and 33 was measured as described in Experimental Example 1, and the results are presented in Table 4 below.

The stability was evaluated for each tablet prepared in Test Samples 22-33, which contained different excipients. After storing each tablet at 50° C. at a closed state for 2 and 4 weeks without controlling RH, the content (%) of M1 Impurity and the content (%) of the total impurities in each tablet were measured according to the HPLC method as described in Experimental Example 1. Table 4 show the results.

TABLE 4

| | | Test Samples | | | | | | | | | | | |
|---|---|---|---|---|---|---|---|---|---|---|---|---|---|
| Function | Ingredient | 22 | 23 | 24 | 25 | 26 | 27 | 28 | 29 | 30 | 31 | 32 | 33 |
| Active ingredient | hydrochloric acid salt of Compound 1 | 21.8 | 21.8 | 21.8 | 21.8 | 21.8 | 21.8 | 21.8 | 21.8 | 21.8 | 21.8 | 21.8 | 21.8 |
| Diluent | lactose hydrate (Flowlac 100) | 269.2 | 254.2 | 254.2 | 239.2 | 254.2 | 239.2 | 254.2 | 239.2 | 254.2 | 239.2 | 254.2 | 239.2 |
| Binder | HPC EXF | 3 | 3 | 3 | 3 | 3 | 3 | 3 | 3 | 3 | 3 | 3 | 3 |
| Disintegrant | Low-Substituted Hydroxypropyl Cellulose | — | — | 15 | 15 | — | — | — | — | — | — | — | — |
| Disintegrant | Corn starch | — | — | — | — | 15 | 15 | — | — | — | — | — | — |
| Disintegrant | polacrilin potassium | — | — | — | — | — | — | 15 | 15 | — | — | — | — |
| — | CMC-Ca | — | — | — | — | — | — | — | — | 15 | 15 | | |
| — | CMC-Na | — | — | — | — | — | — | — | — | — | — | 15 | 15 |
| Lubricant | colloidal silicon dioxide | 3 | 3 | 3 | 3 | 3 | 3 | 3 | 3 | 3 | 3 | 3 | 3 |
| Lubricant | magnesium stearate | 3 | 3 | 3 | 3 | 3 | 3 | 3 | 3 | 3 | 3 | 3 | 3 |
| pH control agent | fumaric acid | — | 15 | — | 15 | — | 15 | — | 15 | — | 15 | — | 15 |
| — | Total amount of one tablet (mg) | 300 | 300 | 300 | 300 | 300 | 300 | 300 | 300 | 300 | 300 | 300 | 300 |
| | pH measured in an 1% w/v Aqueous Suspension | 6.55 | 2.85 | 6.75 | 2.81 | 6.76 | 2.81 | 7.79 | 3.23 | 5.57 | 2.99 | 7.0 | 3.06 |
| M1 Impurity (%) Closed, 50° C. | Initial | ND | ND | ND | ND | ND | ND | ND | ND | ND | ND | ND | ND |
| | 2 week | 0.29 | 0.02 | 0.46 | 0.05 | 0.60 | 0.04 | 0.83 | 0.24 | 0.28 | 0.05 | 0.68 | 0.04 |
| | 4 week | 0.35 | 0.04 | 0.64 | 0.06 | 0.86 | 0.07 | 1.09 | 0.35 | 0.48 | 0.09 | 1.01 | 0.10 |
| Total | Initial | 0.05 | 0.06 | 0.08 | 0.06 | 0.05 | 0.05 | 0.04 | 0.04 | 0.06 | 0.06 | 0.05 | 0.05 |

TABLE 4-continued

| | | Test Samples | | | | | | | | | | |
|---|---|---|---|---|---|---|---|---|---|---|---|---|
| Function | Ingredient | 22 | 23 | 24 | 25 | 26 | 27 | 28 | 29 | 30 | 31 | 32 | 33 |
| impurities (%) Closed, 50° C. | 2 week | 0.42 | 0.12 | 0.57 | 0.24 | 0.69 | 0.23 | 0.98 | 0.44 | 0.36 | 0.34 | 0.81 | 0.27 |
| | 4 week | 0.53 | 0.16 | 0.8 | 0.35 | 1.04 | 0.41 | 1.49 | 0.77 | 0.62 | 0.56 | 1.28 | 0.47 |

※ ND: Not Determined

The results above show improved stability for compositions of the present invention having a pH of 2.8 to 6.55. In fact, excluding Test Sample 28, the remaining Test Samples were stable. In particular, the test samples where a pH control agent was used to bring the pH to about 3, i.e., Test Samples 23, 25, 27, 29, 31, and 33, showed significantly improved stability.

Experimental Example 4: Stability of Film-Coated Tablet Based on Different Excipients of Test Samples 34 to 36

Based on the preparation methods described in Test Samples 1 to 9, a hydrochloric acid salt of the present compound and each additive were mixed according to the composition shown in Table 5 below, tableted to prepare a tablet (plain), film-coated with Opadry®, to prepare film-coated tablet of Test Samples 34 to 36.

The stability of each tablet prepared in Test Samples 34 to 36 was evaluated. Each tablet was stored at 40° C. at 75% RH with Alu-Alu packaging for 3 months and 6 months in a sealed stated and then the M1 Impurity content (%) and the total impurities content (%) in each a tablet was determined by HPLC according to Experimental Example 1. Table 5 shows the results.

The stability of a film coated pharmaceutical composition comprising an active pharmaceutical ingredient of Formula 1 or a pharmaceutically acceptable salt thereof and at least one pharmaceutically acceptable excipient was confirmed, when the composition had a pH in the range of about 2.6 to about 6.74 when measured in a 1% w/v Aqueous Suspension prepared according to Experimental Example 1.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

TABLE 5

| | Test Samples | | | | | |
|---|---|---|---|---|---|---|
| | 34 | | 35 | | 36 | |
| | Amount of Compound 1 | | | | | |
| | 10 mg | | 20 mg | | 40 mg | |
| Ingredient | mg/tab | % w/w | mg/tab | % w/w | mg/tab | % w/w |
| Core | | | | | | |
| hydrochloric acid salt of Compound 1 | 10.9 | 7.27 | 21.8 | 7.27 | 43.6 | 7.27 |
| lactose hydrate | 127.1 | 84.73 | 254.2 | 84.73 | 508.4 | 84.73 |
| hydroxypropyl cellulose | 1.5 | 1 | 3 | 1 | 6 | 1 |
| carmellose | 7.5 | 5 | 15 | 5 | 30 | 5 |
| colloidal silicon dioxide | 1.5 | 1 | 3 | 1 | 6 | 1 |
| magnesium stearate | 1.5 | 1 | 3 | 1 | 6 | 1 |
| Total amount of core | 150 | 100 | 300 | 100 | 600 | 100 |
| Tablet coating | | | | | | |
| Opadry ® white, 03B28796 | 5 | 3.33 | 10 | 3.33 | 20 | 3.33 |
| Purified water | 45 | — | 90 | — | 180 | — |
| Total amount of a coated tablet | 155 | | 310 | | 620 | |
| pH measured in an 1% w/v Aqueous Suspension | 4.77 | | 4.74 | | 4.78 | |
| M1 impurity (%) Initial | 0 | | 0 | | 0 | |
| Alu-Alu packaging, 40° C./75% RH  3 months | 0.2 | | 0.2 | | 0.1 | |
| 6 months | 0.2 | | 0.2 | | 0.3 | |

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The invention claimed is:

1. A pharmaceutical composition comprising a compound of Formula 1 below or a pharmaceutically acceptable salt thereof as an active ingredient; and at least one pharmaceutically acceptable excipient,
   wherein the pharmaceutically acceptable excipient is a diluent, a binder, a disintegrant, a lubricant, a pH control agent, or any combination thereof;
   wherein the diluent is contained in an amount from about 40 to about 90 wt % based on a total weight of the composition;
   wherein the binder is from about 0.1 to about 30 wt % based on the total weight of the composition;
   wherein the disintegrant is contained in an amount from about 1 to about 40 wt % based on the total weight of the composition;
   wherein the lubricant is contained in an amount from about 0.5 to about 40 wt % based on the total weight of the composition; and
   wherein the pH control agent is contained in an amount from about 0.01 to about 20 wt % based on the total weight of the composition,
   wherein the disintegrant is selected from the group consisting of crospovidone, croscarmellose sodium, sodium starch glycolate, carboxymethylcellulose (CMC), CMC-Ca, CMC-Na, low substituted hydroxypropyl cellulose, corn starch, and polacrilin potassium, or any combination thereof,
   wherein the diluent is selected from the group consisting of lactose hydrate, anhydrous lactose, mannitol, sorbitol, microcrystalline cellulose, dibasic calcium phosphate hydrate, or any combination thereof;
   wherein the binder is selected from the group consisting of hydroxypropyl cellulose (HPC) and povidone, or any combination thereof;
   wherein the lubricant is selected from the group consisting of colloidal silicon dioxide, magnesium stearate, sodium stearyl fumarate, talc, stearic acid or any combination thereof; and
   wherein the pH control agent is selected from the group consisting of citric acid, fumaric acid, maleic acid, or any combination thereof, and
   wherein the pharmaceutical composition has a pH of about 2.8 to about 6.55 measured in 1% w/v aqueous suspension:

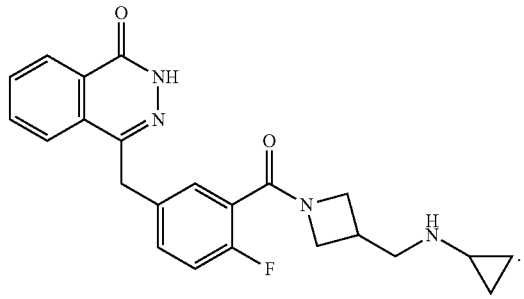

<Formula 1>

2. The pharmaceutical composition according to claim 1, wherein the active ingredient is a hydrochloric acid salt of the compound of Formula 1.

3. The pharmaceutical composition according to claim 1, wherein the diluent is selected from the group consisting of lactose hydrate, anhydrous lactose, and microcrystalline cellulose.

4. The pharmaceutical composition according to claim 1, wherein the diluent is lactose hydrate, microcrystalline cellulose, or a mixture thereof.

5. The pharmaceutical composition according to claim 1, wherein the binder is hydroxypropyl cellulose, povidone, or a mixture thereof.

6. The pharmaceutical composition according to claim 1, wherein the disintegrant is selected from the group consisting of low substituted hydroxypropyl cellulose, corn starch, polacrilin potassium, and carmellose.

7. The pharmaceutical composition according to claim 1, wherein the disintegrant is carmellose.

8. The pharmaceutical composition according to claim 1, wherein the lubricant is selected from the group consisting of colloidal silicon dioxide and magnesium stearate.

9. The pharmaceutical composition according to claim 1, wherein the pH control agent has a pH of about 1 to about 5.

10. The pharmaceutical composition according to claim 1, further comprising a superdisintegrant.

11. The pharmaceutical composition according to claim 10, wherein the pharmaceutical composition comprises from about 0.01 to about 20 wt % of the superdisintegrant based on the total weight of the composition.

12. The pharmaceutical composition according to claim 11, wherein the superdisintegrant is selected from the group consisting of crospovidone, croscarmellose sodium, sodium starch glycolate, or any combination thereof.

13. The pharmaceutical composition according to claim 1, wherein the pharmaceutical composition comprises from about 10 mg to about 240 mg of the active ingredient per unit dosage.

14. The pharmaceutical composition according to claim 1, wherein the pharmaceutical composition is in a solid form.

15. The pharmaceutical composition according to claim 14, wherein the solid form is selected from the group consisting of a tablet, wet granules, dry granules, microgranules, or a capsule.

16. The pharmaceutical composition according to claim 1, wherein the solid form is a tablet.

17. The pharmaceutical composition according to claim 16, wherein the solid form is a film-coated tablet.

18. The pharmaceutical composition according to claim 16, wherein the solid form is an enteric-coated tablet.

19. The pharmaceutical composition according to claim 1, wherein the pharmaceutical composition comprises 0.50 wt % or less of an impurity of the active ingredient after 1 month of storage at 20° C. and 75% relative humidity.

20. A stable solid oral dosage form comprising:
a pharmaceutically acceptable excipient and a compound of Formula I:

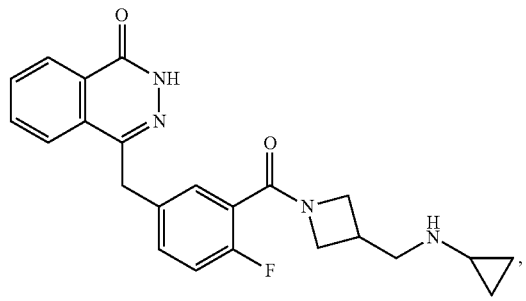

or a pharmaceutically acceptable salt thereof,
wherein the pharmaceutically acceptable excipient is a diluent, a binder, a disintegrant, a lubricant, a pH control agent, or any combination thereof;
wherein the diluent is from about 40 to about 90 wt % based on a total weight of the composition;
wherein the binder is from about 0.1 to about 30 wt % based on the total weight of the composition;
wherein the disintegrant is from about 1 to about 40 wt % based on the total weight of the composition;
wherein the lubricant is from about 0.5 to about 40 wt % based on the total weight of the composition; and
wherein the pH control agent is from about 0.01 to about 20 wt % based on the total weight of the composition,
wherein the oral dosage form maintains at least 99 wt % of the compound of Formula I upon storage under conditions of 20° C. at 75% relative humidity for at least 1 month, wherein the pharmaceutically acceptable excipient is a diluent, a binder, a disintegrant, a lubricant, or any combination thereof,
wherein the disintegrant is selected from the group consisting of crospovidone, croscarmellose sodium, sodium starch glycolate, carboxymethylcellulose (CMC), CMC-Ca, CMC-Na, low substituted hydroxypropyl cellulose, corn starch, and polacrilin potassium, or any combination thereof;
wherein the diluent is selected from the group consisting of lactose hydrate, anhydrous lactose, mannitol, sorbitol, microcrystalline cellulose, dibasic calcium phosphate hydrate, or any combination thereof;
wherein the binder is selected from the group consisting of hydroxypropyl cellulose (HPC) and povidone, or any combination thereof;
wherein the lubricant is selected from the group consisting of colloidal silicon dioxide, magnesium stearate, sodium stearyl fumarate, talc, stearic acid or any combination thereof; and
wherein the stable solid oral dosage form has a pH of about 2.8 to about 6.55 measured in 1% w/v aqueous suspension.

21. The solid oral dosage form of claim 20, wherein the solid oral dosage form is a tablet.

22. A method for preparing a pharmaceutical composition having a pH of about 2.8 to about 6.55 measured in 1% w/v aqueous suspension, comprising:
(a) mixing a compound of Formula 1 below or a pharmaceutically acceptable salt thereof as an active ingredient, with at least one pharmaceutically acceptable excipients to obtain a blend

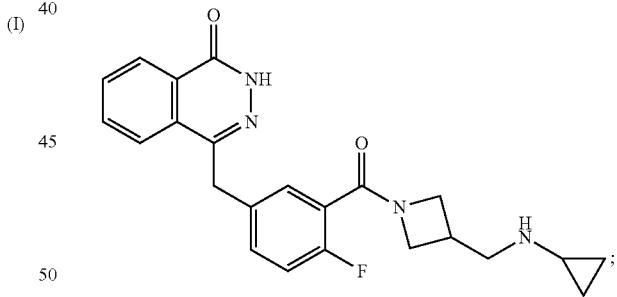

and
(b) directly compressing the blend,
wherein the pharmaceutically acceptable excipient is a diluent, a binder, a disintegrant, a lubricant, a pH control agent, or any combination thereof,
wherein the diluent is from about 40 to about 90 wt % based on a total weight of the composition;
wherein the binder is from about 0.1 to about 30 wt % based on the total weight of the composition;
wherein the disintegrant is from about 1 to about 40 wt % based on the total weight of the composition;
wherein the lubricant is from about 0.5 to about 40 wt % based on the total weight of the composition; and
wherein the pH control agent is from about 0.01 to about 20 wt % based on the total weight of the composition, wherein the disintegrant is selected from the group consisting of crospovidone, croscarmellose sodium, sodium starch glycolate, carboxymethylcellulose (CMC), CMC-Ca, CMC-Na, low substituted hydroxypropyl cellulose, corn starch, and polacrilin potassium, or any combination thereof;

wherein the diluent is selected from the group consisting of lactose hydrate, anhydrous lactose, mannitol, sorbitol, microcrystalline cellulose, dibasic calcium phosphate hydrate, or any combination thereof;

wherein the binder is selected from the group consisting of hydroxypropyl cellulose (HPC) and povidone, or any combination thereof;

wherein the lubricant is selected from the group consisting of colloidal silicon dioxide, magnesium stearate, sodium stearyl fumarate, talc, stearic acid or any combination thereof; and wherein the pH control agent is selected from the group consisting of citric acid, fumaric acid, maleic acid, or any combination thereof.

23. A product obtained from the method of claim 22.

\* \* \* \* \*